United States Patent
Sidor, Jr.

(10) Patent No.: US 6,471,644 B1
(45) Date of Patent: Oct. 29, 2002

(54) ENDOSCOPIC STABILIZATION DEVICE AND METHOD OF USE

(75) Inventor: William E. Sidor, Jr., Rockford, MI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/559,785

(22) Filed: Apr. 27, 2000

(51) Int. Cl.[7] ................................................. A61B 1/32
(52) U.S. Cl. ........................ 600/204; 600/219; 600/235
(58) Field of Search ......................... 600/37, 201, 203, 600/204, 205, 214, 219, 235, 238; 606/190, 191, 198

(56) References Cited

U.S. PATENT DOCUMENTS

| | | | |
|---|---|---|---|
| 1,331,737 A | * 2/1920 | Ylisto | |
| 1,433,031 A | * 10/1922 | Pegaitaz | |
| 3,667,474 A | * 6/1972 | Lapkin et al. | |
| 5,178,133 A | * 1/1993 | Pena | |
| 5,235,966 A | 8/1993 | Jamner | |
| 5,514,075 A | 5/1996 | Moll et al. | 600/202 |
| 5,656,012 A | * 8/1997 | Sienkiewicz | 600/215 X |
| 5,662,676 A | 9/1997 | Koninckx | 606/198 |
| 5,755,661 A | * 5/1998 | Schwartzman | 600/216 |
| 5,807,243 A | * 9/1998 | Vierra et al. | 600/204 |
| 5,891,017 A | * 4/1999 | Swindle et al. | 600/205 |
| 5,927,284 A | 7/1999 | Borst et al. | 128/898 |
| 6,017,342 A | 1/2000 | Rinner | 606/57 |
| 6,152,874 A | * 11/2000 | Looney et al. | 600/214 |
| 6,183,494 B1 | 2/2001 | Amor et al. | 606/198 |
| 6,217,549 B1 | 4/2001 | Selmon et al. | 604/106 |

FOREIGN PATENT DOCUMENTS

DE 4412171 10/1995

\* cited by examiner

*Primary Examiner*—Jeffrey A. Smith
(74) *Attorney, Agent, or Firm*—Thomas G. Berry; Michael J. Jaro; Daniel W. Latham

(57) ABSTRACT

An endoscopic stabilization device is provided. The device includes first and second support elements positioned opposite each other, a plurality of linkages, each linkage including a first end portion attached to the first support element and a second end portion attached to the second support element; and a cable operatively attached to the linkages at a first end to allow a user to pull a second end of the cable to move the first support element in a direction away from the second support element. Methods of using the device to stabilize and immobilize components in the body are also provided.

32 Claims, 3 Drawing Sheets

DEPLOYED CONFIGURATION

DEPLOYMENT CONFIGURATION

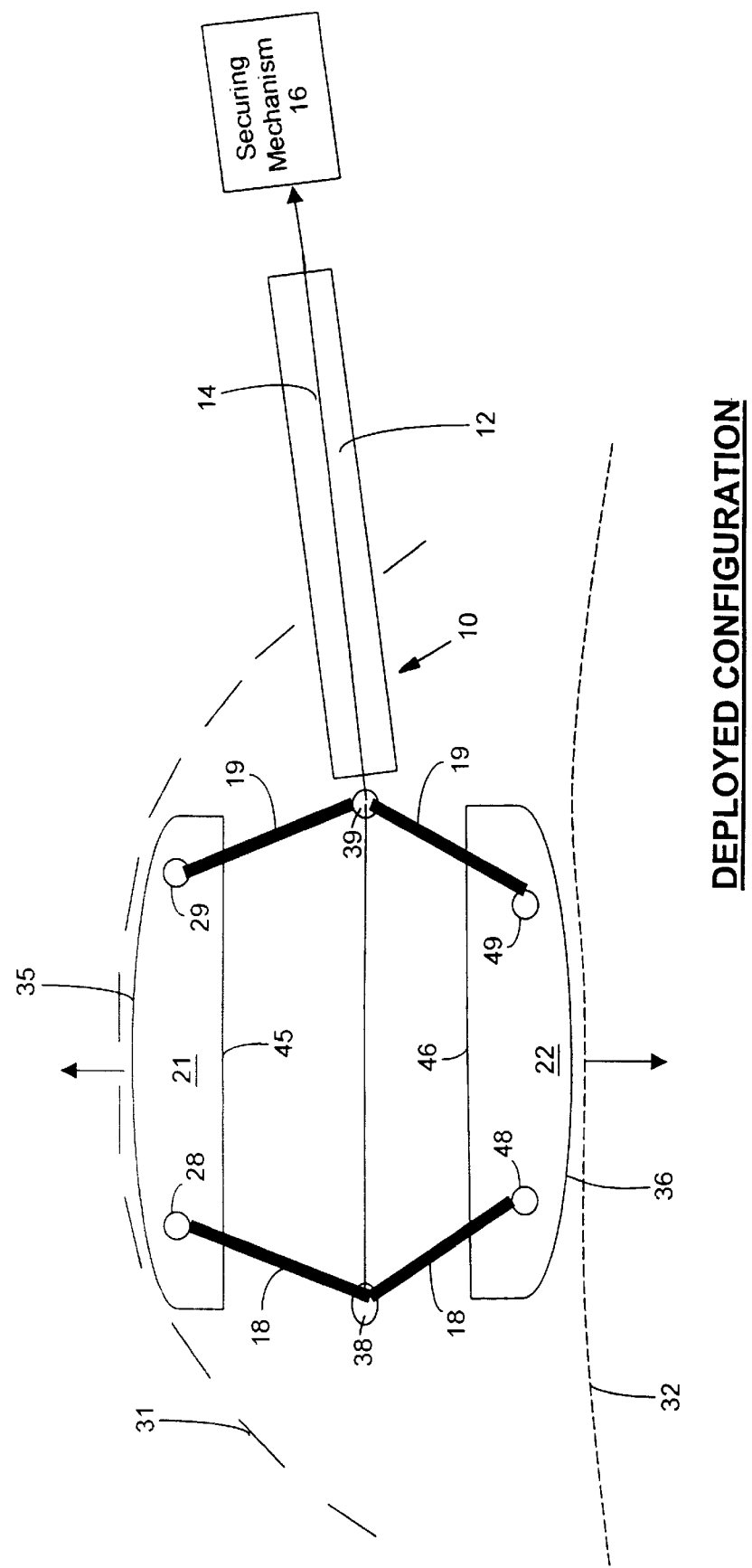

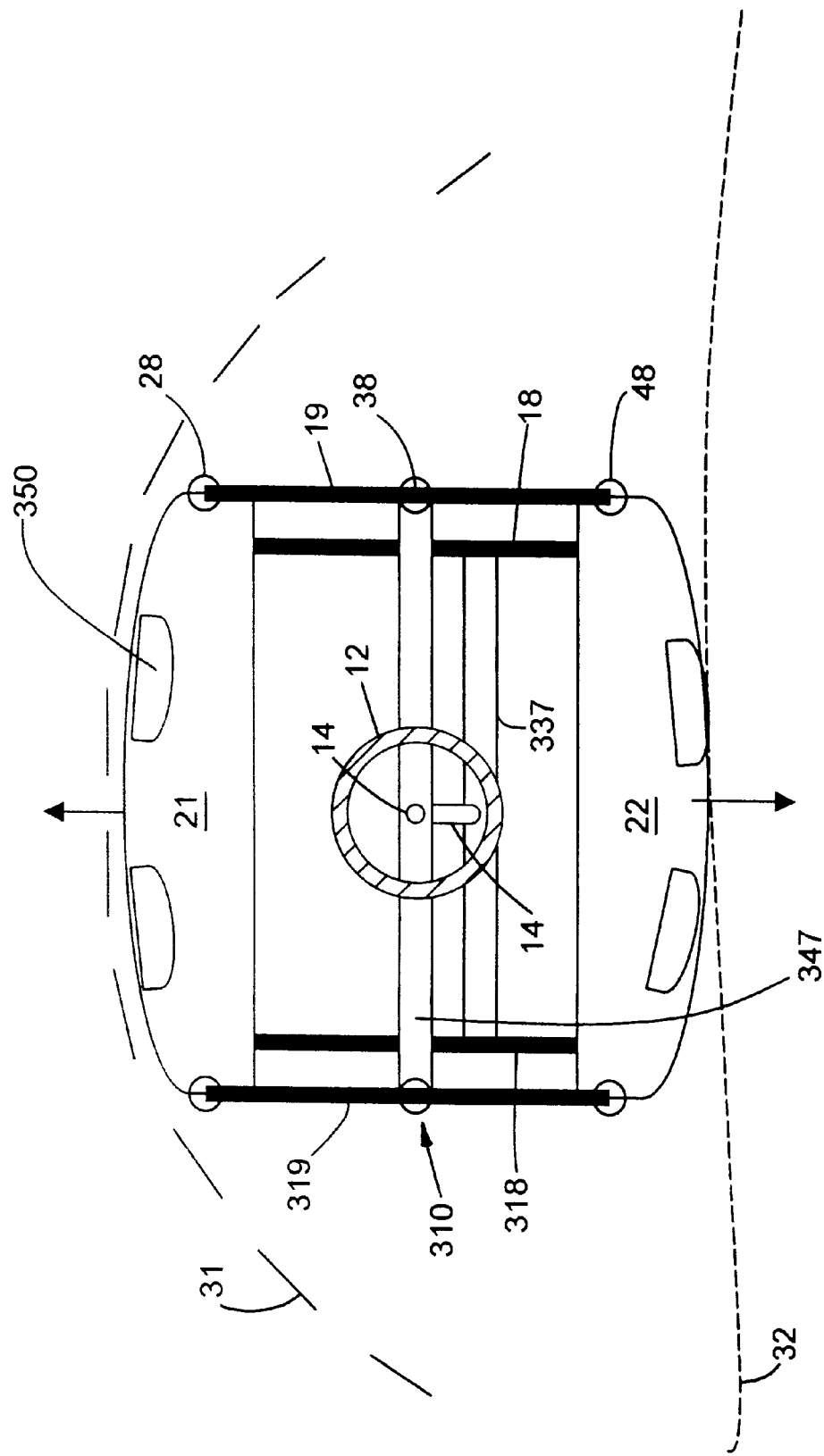

ENDOSCOPIC STABILIZATION DEVICE AND METHOD OF USE

FIELD OF THE INVENTION

This invention relates to devices that are capable of supporting or compressing an organ, such as the heart, and of exposing a given area of tissue to permit a surgical procedure to be performed in an area where minimal invasive procedures are desired. In particular, the invention relates to an endoscopic device that is capable of separating, exposing, stabilizing and supporting different tissues, organs and viscera so that appropriate areas of tissue are exposed.

BACKGROUND OF THE INVENTION

Surgery on certain areas of an organ such as the heart is difficult because the organ is not easily accessible. In particular, as endoscopic surgery becomes more prevalent, the area accessible to surgery will become even more localized. The need for supporting the organ and presenting the appropriate surface for surgery will be even greater. For example, the heart is located beneath the chest wall and surrounded by a variety of other body organs and components, which makes it difficult to access. In addition, the heart continually moves (beats). In order to perform surgery on a particular area of the heart, the heart must be stopped completely or at least stopped in the area of surgery.

Typically, the chest wall is opened and the heart stopped completely for the time it takes the surgery to be performed (open heart surgery.) In some cases, the heart is stopped in particular areas using a device such as the Octopus Cardiac Tissue Stabilizer described in U.S. Pat. No. 5,927,284 to Medtronic. Surgery is then performed in the stopped area while the rest of the heart continues to beat (beating heart surgery). In an endoscopic version of heart surgery, the chest wall would not be opened but rather stab wounds would be made in the chest cavity at strategic points and the surgery performed while the heart remains behind the sternum.

One difficulty in this type of surgery is separating the heart sufficiently from other components within the chest cavity including the sternum and ribs. Another difficulty is stopping the heart in an area to perform the surgery. Although existing devices could be used to immobilize the heart for such surgery, any additional device used must be inserted into the relatively small chest cavity, taking up space.

It would be desirable therefore to have a device that separates the heart sufficiently from other tissues, organs and rib structures to present an area of the heart for surgery without obscuring that area.

Furthermore it would be desirable if the device could also support the heart, bracing it while causing little distress to the heart.

Additionally, it would be desirable if the device could be capable of immobilizing portions of the heart for surgery, thereby eliminating the need for an additional immobilization device, particularly in an endoscopic surgical procedure.

SUMMARY OF THE INVENTION

One aspect of the invention provides an endoscopic stabilization apparatus that includes first and second support elements positioned opposite each other, a plurality of linkages attached to the support elements and a cable attached to the linkages to allow a user to pull the cable to move the first support element in a direction away from the second support element. The apparatus may include a handle portion with an opening for the cable. The apparatus may include a securing mechanism operatively attached to an end of the cable. The first end of the linkages may be attached adjacent an edge of the first support element and the second end of each linkage may be attached adjacent an edge of the second support element. The midpoint of each linkage may also be attached to a connecting bar. The cable is attached in a fixed or a slidable manner at the midpoint of at least one of the linkages. The support elements may be pads arranged directly opposite each other. The support elements may be textured. The support elements may include suction elements. The support elements may return to a collapsed position when the cable is not in tension. The apparatus may be secured with a thumbscrew mechanism.

Another aspect of the invention provides a method of bracing an organ. An endoscopic support apparatus is provided. The apparatus is positioned in a collapsed configuration and inserted into a body cavity. Movement of the cable separates the support elements. At least one of the support elements is then braced against a component within the body cavity. The apparatus may then be secured in a desired configuration. The apparatus may include suction elements that are used to grasp the component within the body cavity.

Another aspect of the invention provides a method of stopping movement of a heart. An endoscopic support apparatus is provided. The apparatus is positioned in a collapsed configuration and inserted into a chest cavity. Movement of the cable separates the support elements. One of the support elements is then braced against an area of chest wall the other is braced against an area of the heart with sufficient pressure to stop movement of the heart. The apparatus may then be secured in a desired configuration. The apparatus may include suction elements that are used to grasp the chest wall and/or the heart.

Another aspect of the invention provides a support apparatus for separating an organ from a chest wall. The apparatus includes an elongated handle including an opening formed therein, a cable received in the handle opening, first and second support elements positioned opposite each other, a first linkage connected adjacent a first end of each of the first and second support elements, a midpoint of the first linkage connected to the cable, a second linkage connected adjacent a second end of each of the first and second support element and a midpoint of the second linkage connected to the cable. The cable is pulled to move the first and second support elements away from each other to separate the organ from the chest wall. The cable is attached in a fixed manner at the midpoint of the first linkage and in a slidable manner at the midpoint of the second linkage. The apparatus may include a securing mechanism attached to an end of the cable.

The foregoing and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 2 is a side view of an endoscopic stabilization device in an expanded position in accordance with the present invention braced within a body cavity; and FIG. 3 is a rear view of another embodiment of an endoscopic stabilization in an expanded position in accordance with the present invention braced within a body cavity.

DETAILED DESCRIPTION OF THE PRESENTLY PREFERRED EMBODIMENTS

Figure 1:
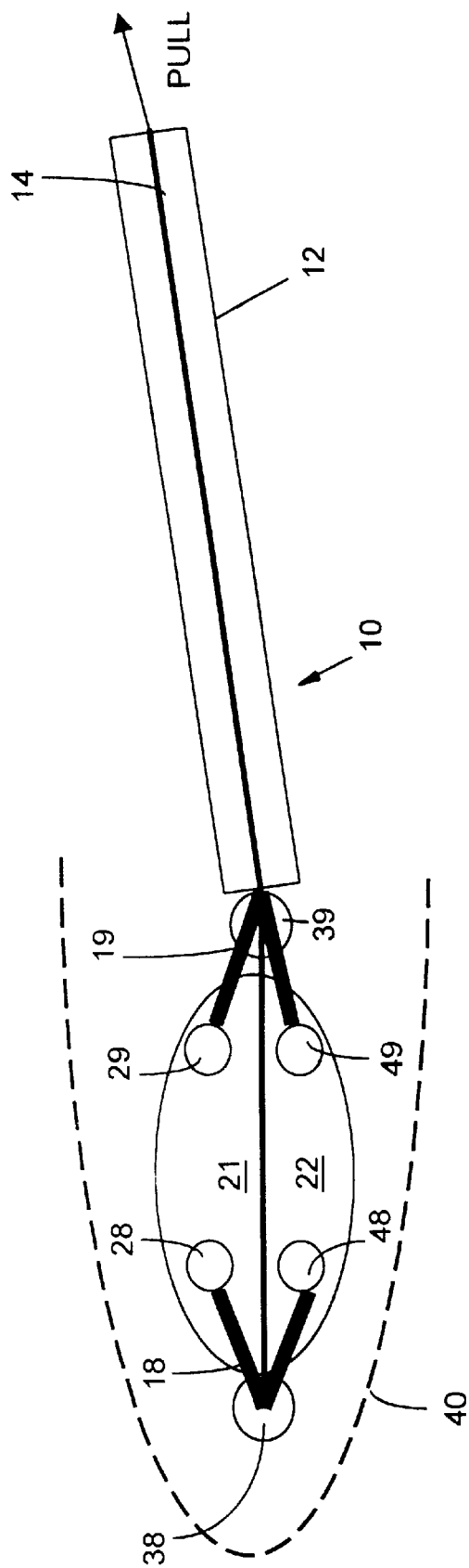
FIG. 1 is a sideview of an endoscopic stabilization device in a collapsed position in accordance with the present invention.

FIG. 1 shows an endoscopic stabilization device in accordance with the present invention in a collapsed configuration. Endoscopic device 10 comprises two support pads 21, 22 arranged one above the other and attached by a connecting cable 14 and an arrangement of rigid linkages 18, 19. The distal end of the connecting cable 14 may be connected to the pad and linkage arrangement. The proximal end of the connecting cable may be enclosed within a hollow handle 12.

The handle 12 of endoscopic device 10 may be a hollow tube of relatively small diameter. Preferably, handle 12 may be a size and diameter insertable within an endoscopic port. For use in a standard endoscopic procedure, for example, the diameter of handle 12 may fall within the range of 2–10 mm. Alternatively, the end of handle 12 that is inserted into the body cavity may be of a smaller diameter than the other end of the handle left outside the body. The diameter of handle 12 may preferably be only slightly larger than the diameter of connecting cable 14.

While it is preferable that handle 12 be circular in cross section, thereby occupying a minimal area, it is contemplated that handle may be square, rectangular or any other cross section that is desired or convenient. Preferably handle 12 may be made of a biocompatible material such as stainless steel, plastic or a combination of the two. Preferably, a biocompatible material prompts little allergenic response from the patient's body and is resistant to corrosion from being placed within the patient's body. Furthermore, the biocompatible material preferably does not cause any additional stress to the patient's body, for example, it does not scrape detrimentally against any elements within the surgical cavity. Handle 12 may be malleable. Optionally, handle 12 may have other components attached to lend convenience and utility to the handle, for example, a grip or trigger component.

Connecting cable 14 may be enclosed within handle 12 such that the two ends of cable 14 protrude from handle 12. The length of connecting cable 14 may be any suitable length for insertion into a body cavity. Cable 14 may have a distal end that is inserted into a body cavity and a proximal end that may be attached to a securing mechanism 16, as seen in FIG. 2. Cable 14 may be made of a biocompatible material as described above. Cable 14 may be a braided metal fiber. Cable 14 may also be a stainless steel cable. Cable 14 is preferably flexible but capable of tensioning without breaking.

At its distal end connecting cable 14 may be connected to an arrangement of rigid linkages 18, 19. These rigid linkages 18, 19 may be disposed between an upper support pad 21 and a lower support pad 22. "Upper" and "lower" are used herein for reference to the figures, and it is contemplated that the device may be used in various orientations. These linkages may be made of stainless steel. Linkages 18, 19 may also be made of a rigid thermoplastic. Alternatively, linkages 18,19 may be made out of any suitably strong, suitably rigid biocompatible material as described above.

Preferably, two rigid linkages 18, 19 may be disposed between pads 21, 22, although the number and configuration of linkages may vary. Linkage 18 may preferably comprise an upper and lower component. "Upper" and "lower" are used herein for reference to the figures, and it is contemplated that the device may be used in various orientations. The upper component of linkage 18 may be attached to upper pad 21 at point 28 and to connecting cable 14 at point 38. The lower component of linkage 18 may be attached to lower pad 22 at point 48 and to connecting cable 14 at point 38. Upper and lower components of linkage 18 may pivot at point 38. Linkage 19 may preferably be structured in the same manner as linkage 18. For example, in FIG. 1, linkage 19 is attached to upper pad 21 at point 29, to connecting cable 14 at point 39 and to lower pad 22 at point 49. Connecting cable 14 may preferably be connected to pivot point 38 in a fixed manner. Connecting cable 14 may preferably be connected to pivot point 39 in a slidable manner.

Upper and lower support pads 21, 22 may be made from biocompatible material. The pads 21, 22 may be made from materials including, for example, thermoplastic or thermosetting materials if it is desired to make endoscopic device 10 disposable. Upper and lowers support pads 21, 22 may be, for example, 5–10 mm in width and 20–30 mm in length for convenient insertion through an endoscopic port. The support pads 21, 22 may be made in any size that is convenient depending upon the need.

Additionally, support pads 21, 22 may be made of material to improve their bracing and grasping properties. For example, pads 21, 22 may be made of any material that grasps organ surfaces well, such as for example, biocompatible rubber. Alternatively, pads 21, 22 may be covered or coated with any material that grasps organ surfaces well. Additionally, support pads 21, 22 or the covering may be textured to better grip an organ surface. Support pads 21, 22 may also incorporate elements that would enable better grasping, such as for example, suction elements.

FIG. 2 shows an endoscopic stabilization device in accordance with the present invention in an expanded configuration within the chest cavity. Rigid linkages 18, 19 are shown connecting upper support pad 21 to lower support pad 22. Connecting cable 14 may be connected to linkage 18 at midpoint 38 and to linkage 19 at midpoint 39.

In use, support device 10 may be inserted into a body cavity, for example, the chest cavity, in the collapsed configuration of FIG. 1. Insertion may be through a cannula or trocar (not shown). When device 10 is in a collapsed configuration, the support pads 21, 22 may present a streamlined device that permits a nontraumatic entry of the device into the body.

Additionally, to facilitate insertion, device 10 may be covered with flexible covering 40 as shown in FIG. 1. This membrane 40 may be made of a flexible biocompatible material such as rubber or polyurethane. Covering 40 may serve to cover any protruding parts of device 10 during insertion into the body cavity. Covering 40 may also serve to help device 10 better conform to and grip the organ surface. Alternatively, device 10 may be inserted without any covering, as seen in FIG. 2.

The surgeon may then use handle 12 to maneuver the support pads 21, 22 into position within the body cavity. At the appropriate location, the surgeon may spread support pads 21, 22 so that upper pad 21 is braced against one element within the cavity and lower pad 22 is braced against a second element within the cavity. For example, in the embodiment shown in FIG. 2, pad 21 may be braced against chest wall 31 and pad 22 may be braced against a surface of the heart 32. As shown in FIG. 2, upper support pad 21 may have an outer face 35 that meets the surface of the organ being braced and an inner face 45 that meets lower support pad 22. Lower support pad 22 may have an outer face 36 that meets the surface of the organ being braced and an inner face 46 that meets upper support pad 21.

The pads 21, 22 may be spread apart by pulling on connecting cable 14. When the surgeon pulls on connecting cable 14, midpoint 39 may be pulled towards handle 12. Meanwhile, midpoint 38 may move closer to midpoint 39. As midpoint 38 moves closer to midpoint 39, the upper and lower components of rigid linkage 18 may be forced apart, thereby forcing upper pad 21 away from lower pad 22. Meanwhile, the tension of midpoint 39 against handle 12 may also force the upper and lower components of rigid linkage 19 apart, thereby forcing upper pad 21 away from lower pad 22. Handle 12 may act as a bracing element for midpoint 39. Alternatively, midpoint 39 may be braced against another suitable bracing element. Rigid linkage 19 may also be made suitably rigid to maintain a braced position for midpoint 39. Alternatively, rigid linkage 19 may incorporate a bracing mechanism to maintain a braced position for midpoint 39.

In order to tension connecting cable 14 so that pads 21, 22 are at a desired position, the proximal end of cable 14 may be attached to a securing mechanism 16. Securing mechanism 16 may be attached to handle 12 or it may be a separate member. This holds stabilization and support device 10 in the desired position for stabilizing an organ such as the heart 32 against the chest wall 31. Securing mechanism 16 may be, for example, a thumbscrew mechanism, which may be twisted to pull the connecting cable 14. Securing mechanism 16 may also be a rack and pinion mechanism, which may be turned to pull the connecting cable 14. Connecting cable 14 may be pulled manually until a desired tension is reached and then attached at its proximal end to a securing mechanism such as a support plate or a support pin. Securing mechanism 16 may be any suitable means for holding pads 21, 22 in the desired expanded position.

In one method of employing stabilization and support device 10, cable 14 is pulled until the position of pads 21, 22 applies sufficient pressure to immobilize an area of the organ being braced. This is particularly desirable because it immobilizes the organ without need for inserting an additional immobilization device. For example, when pads 21, 22 are braced in such a manner against heart 32, a nearby area of heart tissue may be immobilized so that surgery may be performed. No further device may be needed for this immobilization. In another embodiment, two devices 10 are used to brace the heart in two locations. The area between the two locations may then be immobilized so that surgery may be performed.

FIG. 3 shows a rear view of an alternate embodiment of an endoscopic stabilization device 310 in accordance with the present invention. In this embodiment, two rigid linkages 18 and 318 are disposed towards a front end of device 310 and two additional linkages 19 and 319 are disposed towards a back end of device 310. Linkages 18 and 318 may be connected by bar 337, which in turn connects to cable 14 extending through handle 12. Bar 337 serves as a pivot point for linkages 18 and 318. Linkages 19 and 319 may also be connected by a similar bar 347. Bar 347 may also serve as a pivot point for linkages 19 and 319.

In use, pads 21, 22 are spread apart by pulling on connecting cable 14. When the surgeon pulls on connecting cable 14, bar 347 is pulled towards handle 12. Meanwhile, bar 337 moves closer to bar 347. As bar 337 moves closer to bar 347, the upper components of rigid linkages 18, 318 are forced away from the lower components of rigid linkages 18, 318, thereby forcing upper pad 21 away from lower pad 22. Meanwhile, the tension of bar 347 against handle 12 also forces the upper components of rigid linkages 19, 319 away from the lower components of rigid linkages 19, 319, thereby forcing upper pad 21 away from lower pad 22. The proximal end of cable 14 may be attached to a securing mechanism (not shown) as described above to hold stabilization and support device 310 in a desired position.

FIG. 3 also shows suction elements 350 disposed on pads 21, 22. These elements may allow better gripping of organ surfaces such as chest wall 31 and heart 32. It is contemplated that if support pads 21, 22 incorporate suction elements, a flexible suction tube that may provide suction to the suction elements may also serve as connecting cable 14. Alternatively, a separate suction tube or tubes may be incorporated into handle 12.

As noted above, the endoscopic device 10 of the present invention can be used in an endoscopic heart surgery. It is contemplated that the stabilization and support device of the invention may be used in immobilization or bracing of other organs such as, for example, the liver, the diaphragm or the spleen.

It should be appreciated that the embodiments described above are to be considered in all respects only illustrative and not restrictive. The scope of the invention is indicated by the following claims rather than by the foregoing description. All changes that come within the meaning and range of equivalents are to be embraced within their scope.

I claim:

1. An endoscopic stabilization apparatus comprising:
   first and second support elements positioned opposite each other;
   a plurality of linkages, each linkage including a first end portion attached to the first support element and a second end portion attached to the second support element; and
   a cable operatively attached to the linkages at a first end to allow a user to pull a second end of the cable to move the first support element in a direction away from the second support element;
   further comprising a plurality of suction elements operatively attached to a face of each of the first and second support elements.

2. The apparatus of claim 1 further comprising:
   a handle portion, the handle portion including an opening formed therein to receive the cable.

3. The apparatus of claim 1 further comprising:
   a securing mechanism operatively attached to an end of the cable.

4. The apparatus of claim 1 wherein the plurality of linkages comprises two linkages, the first end portion of each linkage attached adjacent an edge of the first support element and the second end portion of each linkage attached adjacent an edge of the second support element.

5. The apparatus of claim 1 wherein the plurality of linkages comprises at least four linkages, the first end portion of each linkage attached adjacent an edge of the first support element and the second end portion of each linkage attached adjacent an edge of the second support element and the midpoint of each linkage operatively attached to a connecting bar.

6. The apparatus of claim 1 wherein the cable is attached in a fixed manner at a midpoint of at least one of the linkages.

7. The apparatus of claim 1 wherein the cable is attached in a slidable manner at a midpoint of at least one of the linkages.

8. The apparatus of claim 1 wherein the cable is attached in a fixed manner at a first midpoint of a first linkage and in a slidable manner at a second midpoint of a second linkage.

9. The apparatus of claim 1 wherein the first and second support elements comprise pads.

10. The apparatus of claim 1 wherein the first and second support elements are positioned directly opposite each other.

11. The apparatus of claim 1 wherein the first and second support elements are textured.

12. The apparatus of claim 1 wherein the first and second support elements return to a collapsed position when the cable is not in tension.

13. The apparatus of claim 1 wherein the securing mechanism is a thumbscrew mechanism.

14. A method of bracing an organ comprising:
   providing an endoscopic support apparatus comprising first and second support elements positioned opposite each other, a plurality of linkages, each linkage including a first end portion attached to the first support element and a second end portion attached to the second support element; and a cable operatively attached to the linkages at a first end to allow a user to pull a second end of the cable to move the first support element in a direction away from the second support element;
   positioning the apparatus in a collapsed configuration;
   inserting the apparatus in a collapsed configuration into a body cavity;
   separating the support elements by movement of the cable; and
   bracing at least one of the support elements against a component within the body cavity;
   wherein the support elements have a face with a plurality of suction elements operatively attached to the face, further comprising:
      grasping the component within the body cavity with at least one of the suction elements.

15. The method of claim 14 further comprising:
   securing the apparatus into a desired configuration.

16. The method of claim 14, wherein the support elements are textured.

17. A method of stopping movement of a heart comprising:
   providing an endoscopic support apparatus comprising first and second support elements positioned opposite each other, a plurality of linkages, each linkage including a first end portion attached to the first support element and a second end portion attached to the second support element; and a cable operatively attached to the linkages at a first end to allow a user to pull a second end of the cable to move the first support element in a direction away from the second support element;
   positioning the apparatus in a collapsed configuration;
   inserting the apparatus in a collapsed configuration into a chest cavity;
   separating the support elements by movement of the cable;
   bracing the first support element against an area of chest wall; and
   bracing the second support element against an area of the heart with sufficient pressure to stop movement of the heart.

18. The method of claim 17 further comprising:
   securing the apparatus into a desired configuration.

19. The method of claim 17 wherein the support elements are textured.

20. The method of claim 17, wherein the support elements have a face with a plurality of suction elements operatively attached to the face, further comprising:
   grasping the chest wall with at least one of the suction elements.

21. The method of claim 17, wherein the support elements have a face with a plurality of suction elements operatively attached to the face, further comprising:
   grasping the heart with at least one of the suction elements.

22. A support apparatus for separating an organ from a chest wall, comprising:
   an elongated handle including an opening formed therein;
   a cable received in the handle opening;
   first and second support elements positioned opposite each other, the support elements having a face with a plurality of suction elements operatively attached to the face;
   a first linkage connected adjacent a first end of each of the first and second support elements;
   a midpoint of the first linkage connected to the cable;
   a second linkage connected adjacent a second end of each of the first and second support element; and
   a midpoint of the second linkage connected to the cable;
   wherein the cable is pulled to move the first and second support elements away from each other to separate the organ from the chest wall.

23. The apparatus of claim 22 wherein the cable is attached in a fixed manner at the midpoint of the first linkage and in a slidable manner at the midpoint of the second linkage.

24. The apparatus of claim 22 further comprising:
   a securing mechanism operatively attached to an end of the cable.

25. An endoscopic stabilization apparatus comprising:
   first and second support elements positioned opposite each other, the support elements having a face with a plurality of suction elements operatively attached to the face;
   means for movably attaching the first support element to the second support element; and
   cable means operatively attached to the means for movably attaching the first and second support elements for allowing a user to move the first support element in a direction away from the second support element.

26. The apparatus of claim 25 wherein at least a portion of the cable means is slideably received within a handle.

27. The apparatus of claim 25 also comprising a securing mechanism operatively attached to the cable means.

28. A method of surgical treatment of a heart comprising:
   providing an endoscopic support apparatus comprising first and second support elements positioned opposite each other, a plurality of linkages, each linkage including a first end portion attached to the first support element and a second end portion attached to the second support element; and a cable operatively attached to the linkages at a first end to allow a user to pull a second end of the cable to move the first support element in a direction away from the second support element;

making an opening in the chest cavity such that the heart remains behind the sternum;

positioning the apparatus in a collapsed configuration;

inserting the apparatus in a collapsed configuration through the opening into the chest cavity;

separating the support elements by movement of the cable;

bracing the first support element against an area of chest wall; and bracing the second support element against an area of the heart.

29. The method of claim 28 further comprising:

securing the apparatus into a desired configuration.

30. The method of claim 28 wherein the support elements are textured.

31. The method of claim 28 wherein the support elements have a face with a plurality of suction elements operatively attached to the face, further comprising:

grasping the chest wall with at least one of the suction elements.

32. The method of claim 28, wherein the support elements have a face with a plurality of suction elements operatively attached to the face, further comprising:

grasping the heart with at least one of the suction elements.

* * * * *